United States Patent [19]

Socol

[11] Patent Number: 4,547,464

[45] Date of Patent: Oct. 15, 1985

[54] FETAL PULMONARY MATURITY TEST

[76] Inventor: Michael Socol, 4250 N. Marine Dr., Apt. 922, Chicago, Ill. 60613

[21] Appl. No.: 588,537

[22] Filed: Mar. 12, 1984

[51] Int. Cl.$^4$ .................. G01N 33/48; G01N 13/00
[52] U.S. Cl. .................................... 436/2; 436/71; 436/907; 73/60.1; 73/61 R
[58] Field of Search .................. 422/61; 436/63, 71, 436/2, 104, 105, 907; 73/60.1, 61 R

[56] References Cited

PUBLICATIONS

Roux et al., Assessment of Fetal Maturation by the Foam Test, Sep. 15, 1973, *Am. J. Obstet. Gynecol.*

Sher et al., Clinical Evaluation of the Quantitative Foam Stability Index Test, May 1980, *Am. College Obstet. Gynecol.*

Kulovich et al., The Lung Profile I. Normal Pregnancy, Sep. 1, 1979, *Am. J. Obstet. Gynecol.*

Clements et al., Assessment of the Risk of the Respiratory Distress Syndrome by a Rapid Test for Surfactant in Amniotic Fluid, May 18, 1972, *The New England J. of Medicine.*

Torday et al., Saturated Phosphatidylcholine in Amniotic Fluid and Prediction of the Respiratory Distress Syndrome, 11-08-79, *The New England J. of Medicine.*

Tsai et al., Phosphatidylglycerol in 261 Samples of Amniotic Fluid from Normal and Diabetic Pregnancies, as Measured by a One Dimensional Thin Layer Chromotography, 1979, *Clinical Chemistry.*

Olson et al., The Use of Amniotic Fluid Bubble Stability, L/S Ratio and Creatinine Concentration in the Assessment of Fetal Maturity, Jul 15, 1975, *Am. J. Obstet. Gynecol.*

O'Brien et al., Clinical Applicability of Amniotic Fluid Tests for Fetal Pulmonic Maturity, 1-1-1980, *Am. J. Obstet. Gynecol.*

Sher et al., Assessing Fetal Lung Maturation by the Foam Stability Index Test, Dec. 1978, *The Am. College of Obstet. Gynecol.*

Gluck et al., Diagnosis of the Respiratory Distress Syndrome by Amniocentesis, Feb. 1, 1971, *Amer. J. Obstet. Gynecol.*

Collaborative Group, Effect of Antenatal Dexamethasone Administration on the Prevention of Respiratory Distress Syndrome, Oct. 1, 1981, *Am. J. Obstet. Gynecol.*

Zuspan et al., Amniotic Fluid and Fetal Maturity, Jan. 1, 1976, *The Journal of Reproductive Medicine.*

*Primary Examiner*—Barry S. Richman
*Assistant Examiner*—Michael S. Gzybowski
*Attorney, Agent, or Firm*—Welsh & Katz, Ltd.

[57] ABSTRACT

A quick and inexpensive test for the detection of fetal pulmonary maturity comprising the steps of acidifying a given volume of amniotic fluid, adding a given volume of an ether, agitating and observing the number of bubbles existing in the ether layer. The number of bubbles existing in the ether layer after a certain observational period may be correlated with the existence of pulmonary immaturity in a fetus.

8 Claims, No Drawings

FETAL PULMONARY MATURITY TEST

This application relates to the evaluation of fetal maturity and more particularly to a method for the prenatal evaluation of fetal lung maturation.

BACKGROUND OF THE INVENTION

In pregnancies complicated by various factors such as diabetes and other high risk factors or complications, the possibilities of the newborn infant being delivered prior to the development of lungs mature enough to autonomously support respiration may be increased significantly. As a result, reliable tests for the determination of fetal pulmonary maturity are desirable and would eliminate some of the risk in the delivery of such a pulmonarily immature infant. Pulmonary immaturity is commonly referred to as "respiratory distress syndrome" (RDS) and continues to rank as a major public health problem.

Analysis of the amniotic fluid is commonly used as a clinical test of fetal maturity. The most widely accepted method has been to determine the ratio of lecithin and sphingomyelin (L/S ratio). Other more recent studies have advocated the analysis for phosphatidyl glycerol, which is recognized as a potent phospholipid and surfactant in the amniotic fluid and is generally analyzed by a thin layer chromotography method.

Other phospholipids have also been measured with chromatography as a means for predicting the risk of RDS.

It is now widely agreed that RDS in infants is brought on by the collapse of the pulmonary alveoli. The resistance of pulmonary alveoli to collapse during expiration has been shown to be due to the presence of a surfactant, i.e., a substance which lowers surface tension in the alveoli. It has subsequently been confirmed that a surfactant is secreted into the alveoli, and further that the production and secretion of surfactant into the alveoli is dependent upon reaching a certain gestational age, i.e., maturity.

Pulmonary surfactant development also correlates with the stability of bubbles in amniotic fluid mixed with ethanol, a diluent in a solution which is used in a test known as a Foam Stability Index (FSI) test.

The above named method of analysis of fetal pulmonary maturity measures the stability or life of bubbles in an amniotic fluid solution. The FSI test includes a combination of amniotic fluid and ethanol shaken vigorously for thirty seconds, and observation of the existence or nonexistence of an uninterrupted ring of bubbles at the air-fluid interface around the meniscus of the test tube, following a settling period of fifteen or more seconds after shaking. This test, while generally providing reliable positive results, is found to yield false negative results and therefore cannot be completely accurate in screening for immature fetal pulmonary function. When compared with the L/S test, which takes several hours, much expertise and sophisticated instruments to perform, and further, is not usually available on a twenty-four emergency basis, the FSI test is far superior. The FSI test is much simpler, is not dependent on the availability of sophisticated equipment and can be performed and analyzed in less than thirty minutes. However, the reliability of the foam stability test depends greatly on the addition of precise amounts of both the amniotic fluid and the alcohol. As a result the test must be performed under controlled conditions, and, even when so conducted, the test results do not reliably predict immature lung function.

In view of the above current test procedures for fetal pulmonary maturity, the ideal test should be rapid and inexpensive, yet have a high accuracy or predictive level for both mature and immature pulmonary function.

SUMMARY OF THE INVENTION

Therefore, an object of the invention is an improved and accurate test for the assessment of fetal pulmonary maturity.

A further object of the subject invention is an improved bedside test for accurately predicting the maturity or immaturity of fetal lung capacity.

A still further object of the subject invention is a simple diagnostic test comprising the combination of amniotic fluid with acidified ether, with continuing observation, all capable of being performed in a relatively short period of time without precise measurement and at the patient's bedside.

These and other objects are provided in furtherance of the subject invention wherein there is taught a method for conducting a foam stability test having the steps of obtaining amniotic fluid by amniocentesis or other method during human gestation. The foam stability test is conducted by mixing the amniotic fluid with a concentrated inorganic acid solution followed by addition of an alkyl ether, all in a test tube. The test tube is briskly tapped to create bubbles in the ether layer. The determination of fetal maturity may be made by the observation of bubbles after a short period of time. When the results of the subject invention are compared with those predicted by a phospholipid profile as well as the actual observation of fetal pulmonary immaturity in the delivered newborn babies, an accurate predictive test is noted which can be quickly performed at a patient's bedside, without a great deal of attention to precision in measurement of the solution or test components.

DETAILED DESCRIPTION OF THE INVENTION

In the diagnostic test of the subject invention fetal pulmonary maturity is assessed based on a qualitative analysis of the properties of the amniotic fluid drawn from the mother of the fetus in concern. Amniotic fluid may be obtained by amniocentesis, hind water amniotomy (performed with a Drew Smythe catheter), or from a freely flowing vaginal pool under appropriate conditions. One millimeter of amniotic fluid is blended with one drop (generally 1/20th of a milliliter) of a inorganic acid solution. Approximately 1.5 milliliters of an alkyl ether is then added to the test tube, which is briskly tapped with a finger three or four times, thereby creating an estimated 200 to 300 bubbles in the ether (upper) layer. These bubbles in the ether layer are observed for a period of from 2 to 10 minutes. At the end of the observation period the number of bubbles was counted. If 5 or less bubbles persisted in the ether layer, the test was considered to indicate maturity in the pulmonary function of the infant. If more than 5 bubbles exist in the ether layer at the end of the observation period, such number was considered to indicate immaturity of the fetus. The occasional bubbles which may have been confined to the amniotic fluid layer were ignored.

In forming the test solution it should be stressed that sufficient inorganic acid such as sulfuric acid, hydrochloric acid, nitric acid and the like should be used in sufficient concentrations and quantities to acidify the amniotic fluid solution. In addition, the ether should be an alkyl ether such as diethyl ether which is stable under acidic conditions such as are used in the subject test. It is necessary that the ether used be of low viscosity, and also be relatively immiscible with the amniotic fluid. Such immiscibility should be sufficient to maintain substantially separate layers of ether and amniotic fluid upon the slight agitation occassioned by tapping with the fingers. Ethyl ether has been found preferable, being of the required low viscosity and immiscibility with the amniotic fluid layer. Other ethers may be used and may indeed be found preferable in part due to their less flammable nature. The manner of agitation of the test tube set forth herein as being through finger tapping may be occasioned through any similar means such as shaking in a back and forth motion a few times or the like. While a mechanical shaker may be used to impart identical shaking motions each time, such is not considered necessary to achieve equivalent and consistent results.

It is intended that the scope of this invention include a self-contained kit for performing the test of the subject invention. This kit might include a pre-scaled test tube having a pre-measured amount of acid within and under a slight negative pressure. Dependent on other factors it may be desirable to also include at the point of assembly a premeasured volume of ether in the test tube or other container. The test tube may be sealed with a closure such as a rubber septum or the like as normally found in blood collection tubes. However, other more simple closures, such as screw-on caps may be used, providing a fluid tight seal can be maintained. In such a case, no vacuum in the container need be present. The amniotic fluid may be drawn into a syringe, which may also be used for measuring a relatively exact amount of amniotic fluid to be injected into the tube at bedside. If not already included in the tube, ether may be added to the acidified amniotic fluid in the test tube at the time of performing the test via the same manner, e.g., a syringe. Because the tube is under negative pressure, i.e., a slight vacuum, the addition of the amniotic fluid and ether do not disturb the septum seal. Such a kit could take other forms as well.

The following examples illustrate the practice of the test method and results of the subject invention, and are not to be taken as limiting in any respect. All parts and percentages unless expressly stated to be otherwise, are by volume. All of the below tests were performed by a single investigator who was unaware of the patient's clinical course. The amniotic fluid was obtained by resident house staff, either by amniocentesis or from a freely flowing vaginal pool. If the tap test or phospholipid profile could not be run immediately, the amniotic fluid was refrigerated. However, all amniotic fluid was analyzed within twenty-four hours of procuring. Prior to use any amniotic fluid which was contaminated by blood or meconium was spun for five minutes in a tabletop centrifuge at 400×g. Vaginal pool amniotic fluid was similarly treated to remove any contaminating mucus. Clear amniotic fluid obtained by amniocentesis was not centrifuged.

The phospholipid profile used for comparison purposes with the test of the subject invention was performed in a hospital chemistry laboratory by one-dimensional planimetric thin layer chromatography following centrifugation for five minutes at 800×g and acetone precipitation. An L/S or lecithin/sphingomyelin ratio of 2:1 or greater or the presence of phosphatidylglycerol was considered mature.

Only deliveries which occurred within seventy-two hours of obtaining the amniotic fluid specimen are reported. The sensitivity, specificity, and predictive values for the test of the subject invention and phospholipid profile were determined by comparing the results of those tests to the absence or presence of the neonatal respiratory distress syndrome (RDS). The diagnosis of RES was made by the attending neonatalogist and was based on standard clinical blood gas and radiologic findings. These include chest retraction, grunting, cyanosis, oxygen supplementation for a minimum of twenty-four hours, and a ground glass appearance with air bronchograms on chest x-ray. Gestational age was determined by the best fit of menstrual dates, ultrasound if available and Dubowitz examination.

TABLE I

| | Gestational Age Distribution | | |
|---|---|---|---|
| Weeks | RDS | No RDS | Total |
| 26–27 | 2 | 1 | 3 |
| 28–30 | 5 | 2 | 7 |
| 31–33 | 7 | 19 | 26 |
| 34–36 | 1 | 33 | 34 |
| 37 or greater | 0 | 18 | 18 |
| | 15 | 73 | 88 |

Preterm delivery of fetuses may be defined by delivery of the fetus less than 37 weeks of gestation. Thus, through the above Table, it can be seen that 80% (70/88) of the fetuses studied in the following test were delivered preterm as defined above.

TABLE II

| Comparison of Tap Test vs. Phospholipid Profile | | | | |
|---|---|---|---|---|
| | Observational Period | True Mature | False Mature | True Immature | False Immature |
| Clear AF | | | | | |
| Tap Test | 2 min. | 39 | 0 | 8 | 11 |
| | 5 min. | 43 | 0 | 8 | 7 |
| | 10 min. | 44 | 0 | 8 | 6 |
| Phospholipid Profile | | 37 | 0 | 8 | 13 |
| Blood Tinged | | | | | |
| Tap Test | 2 min. | 6 | 0 | 3 | 2 |
| | 5 min. | 6 | 0 | 3 | 2 |
| | 10 min. | 7 | 0 | 3 | 1 |
| Phospholipid Profile | | 5 | 0 | 3 | 3 |
| Meconium Stained | | | | | |
| Tap Test | 2 min. | 2 | 0 | 0 | 0 |
| | 5 min. | 2 | 0 | 0 | 0 |
| | 10 min. | 2 | 0 | 0 | 0 |
| Phospholipid Profile | | 2 | 0 | 0 | 0 |
| Vaginal Pool | | | | | |
| Tap Test | 2 min. | 6 | 0 | 4 | 7 |
| | 5 min. | 9 | 1 | 3 | 4 |
| | 10 min. | 10 | 1 | 3 | 3 |
| Phospholipid Profile | | 5 | 1 | 3 | 8 |
| Total Population | | | | | |
| Tap Test | 2 min. | 53 | 0 | 15 | 20 |
| | 5 min. | 60 | 1 | 14 | 13 |
| | 10 min. | 63 | 1 | 14 | 10 |
| Phospholipid Profile | | 49 | 1 | 14 | 24 |

Key
True mature: predicted mature, no RDS
False mature: predicted mature, RDS
True immature: predicted immature, RDS
False immature: predicted immature, no RDS The above Table II sets forth the results of the test of the subject invention, referred to simply as the "tap test" in these tables after observational periods of 2, 5 and 10 minutes, and the phospholipid profile for each of the noted amniotic fluid samples. The results of both the test of the subject invention and the phospholipid profile test are analyzed further in Table III below. As can be seen from Table III, the predictive value for a mature tap test from clear amniotic fluid obtained by amniocentesis was 100% at all times of observation. Predictive values for an immature test were between 40-60%. These results may be compared with the phospholipid profile which had predictive values for mature tests of 100% and an immature test of approximately 38%.

TABLE III

Sensitivity, Specificity, and Predictive Values for the Tap Test and Phospholipid Profile

|  | Tap Test 2 min. | Tap Test 5 min. | Tap Test 10 min. | Phospholid Profile |
|---|---|---|---|---|
| Clear AF | | | | |
| Sensitivity | 100 (8/8) | 100 (8/8) | 100 (8/8) | 100 (8/8) |
| Specificity | 78 (39/50) | 86 (43/50) | 88 (44/50) | 74 (37/50) |
| Predictive Value | | | | |
| Mature | 100 (39/39) | 100 (43/43) | 100 (44/44) | 100 (37/37) |
| Immature | 42 (8/19) | 53 (8/15) | 57 (8/14) | 38 (8/21) |
| Total Population | | | | |
| Sensitivity | 100 (15/15) | 93 (14/15) | 93 (14/15) | 93 (14/15) |
| Specificity | 73 (53/73) | 82 (60/73) | 86 (63/73) | 67 (49/73) |
| Predictive Value | | | | |
| Mature | 100 (53/53) | 98 (60/61) | 98 (63/64) | 98 (49/50) |
| Immature | 43 (15/35) | 52 (14/27) | 58 (14/24) | 37 (14/38) |

Sensitivity = $\frac{\text{correctly predicted immature}}{\text{all immature}}$

Specificity = $\frac{\text{correctly predicted mature}}{\text{all mature}}$

Predictive value, mature = $\frac{\text{correctly predicted mature}}{\text{all predicted mature}}$ Predictive value, immature = $\frac{\text{correctly predicted immature}}{\text{all predicted immature}}$ When the entire population is analyzed, the predictive values for mature tap test vary from 98-100% at all times of observation. The predictive values for an immature test range from 43-58% using the test of the subject invention. The phospholipid profile by comparison had predictive values for mature pulmonary function of 98% and for immature pulmonary function of 37%.

The ability of the test of the subject invention utilizing the five minute observation period to correctly predict the absence of RDS is compared to that of the phospholipid profile in Table IV below. Predictions of the two tests differed in twenty-one of the seventy-three fetuses which did not develop RDS. The test of the subject invention indicated that the lungs were mature in sixteen fetuses, while the phospholipid profile predicted maturity in the other five. This difference is statistically significant. While the ten minute observation period for the test of the subject invention was also a better predictor of the absence of RDS than the phospholipid profile, the two minute observation period for the test of the subject invention was comparable to the phospholipid profile. Each of the two, five, and ten minute periods of observation in the test of the subject invention were comparable to the phospholipid profile test in predicting the presence of RDS. Reproducibility has been assessed by performing the test of the subject invention in duplicate on a number of patients. Out of forty-five patients tested in duplicate, only three differed in result; the interpretations of these three tests being borderline, with only six to twenty bubbles remaining at five minutes.

TABLE IV

Five Minute Tap Test vs. Phospholipid Profile in Fetuses Not Developing RDS

| | Phospholipid Profile | | |
|---|---|---|---|
| Tap Test | Mature | Immature | Total |
| Mature | 44 | 16* | 60 |
| Immature | 5* | 8 | 13 |
| Total | 49 | 24 | 73 |

*p <.02, exact test

In addition, various random samples of amniotic fluid were centrifuged and compared with aliquots of the same sample which had not been centrifuged and the results at five minutes of observation period showed no differences in interpretation between the centrifuged and the uncentrifuged samples.

By the test of the subject invention for the analysis of amniotic fluid in the determination of fetal pulmonary immaturity, a rapid, inexpensive, bedside test is available. In addition, only a small amount, i.e., one milliliter of amniotic fluid is required. The predictive values of the test of the subject invention are comparable with or better than the phospholipid profile test which must be run in a laboratory with expensive and time consuming procedures. The test of the subject invention has been shown to be reproducible, yet semi-quantitative in terms of measurement of the reactants and observation of the results.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A method for testing for fetal pulmonary immaturity comprising the steps of withdrawing amniotic fluid from a pregnant mother, acidifying a predetermined amount of said amniotic fluid, adding an approximately equal volume of an alkyl ether to form a testing solution having an ether layer over an amniotic fluid layer; agitating said testing solution sufficiently to create a multitude from about 200 to 300 of bubbles in said ether layer, permitting said agitated testing solution to rest for an observational period of at least 2 minutes, observing the number of bubbles remaining in said ether layer after the passage of said observational period, and from said number of remaining bubbles predicting the maturity or immaturity of the fetal pulmonary function of the fetus within the womb of the pregnant mother.

2. The method of claim 1 wherein one milliliter of amniotic fluid is mixed with a drop of an inorganic acid to form an acidified amniotic fluid solution; and approximately 1.5 milliliters of diethyl ether is added to said acidified amniotic fluid solution.

3. The method of claim 1 wherein the test solution is agitated by briskly tapping the container holding the said test solution 3 or 4 times with a finger.

4. The method of claim 1 wherein the prediction of fetal pulmonary maturity is accomplished through the observation of no more than five bubbles in the ether layer after passage of said observation period.

5. The method of claim 1 wherein said observational period is 2 minutes, 5 minutes or 10 minutes.

6. A method for testing for fetal pulmonary immaturity comprising the steps of:
   (1) withdrawing amniotic fluid from a pregnant mother;
   (2) adding one drop of hydrochloric acid to acidify approximately 1.0 milliliter of said amniotic fluid in a test tube;
   (3) adding approximately 1.5 milliliters of ethyl ether to form a testing solution in said test tube having an ether layer over an amniotic fluid layer;
   (4) agitating said testing solution by tapping said test tube to create a multitude from about 200 to 300 of bubbles in said ether layer;
   (5) permitting said agitated testing solution to rest for an observational period of at least 2 minutes;
   (6) observing the number of bubbles remaining in said ether layer after the passage of said observational period; and
   (7) from said number of remaining bubbles predicting the maturity or immaturity of the fetal pulmonary function of the fetus within the womb of the pregnant mother.

7. The method of claim 6 wherein the prediction of fetal pulmonary maturity is accomplished through the observation of no more than five bubbles in the ether layer after passage of said observation period.

8. The method of claim 6 wherein said observational period is 2 minutes, 5 minutes or 10 minutes.

* * * * *